US012677818B2

(12) United States Patent     (10) Patent No.:   US 12,677,818 B2

Camarero Díez et al.     (45) Date of Patent:     Jul. 14, 2026

(54) DEVICE FOR DIFFUSING VOLATILE SUBSTANCES

(71) Applicant: ZOBELE HOLDING SPA, Trento (IT)

(72) Inventors: Roberto Camarero Díez, Barcelona (ES); Julio Cesar Ruiz Ballesteros, Barcelona (ES); Jessica Sijmons, Barcelona (ES)

(73) Assignee: ZOBELE HOLDING SPA, Trento (IT)

( * ) Notice: Subject to any disclaimer, the term of this patent is extended or adjusted under 35 U.S.C. 154(b) by 609 days.

(21) Appl. No.: 17/414,757

(22) PCT Filed: Dec. 19, 2019

(86) PCT No.: PCT/EP2019/086380

§ 371 (c)(1),
(2) Date: Jun. 16, 2021

(87) PCT Pub. No.: WO2020/127785

PCT Pub. Date: Jun. 25, 2020

(65) Prior Publication Data

US 2022/0063230 A1     Mar. 3, 2022

(30) Foreign Application Priority Data

Dec. 21, 2018    (ES) .................................. 201831264

(51) Int. Cl.
   *A61L 9/12*       (2006.01)
   *A01M 1/20*      (2006.01)
       (Continued)

(52) U.S. Cl.
   CPC ........ *A01M 1/2055* (2013.01); *A01M 1/2044* (2013.01); *A61L 9/12* (2013.01);
       (Continued)

(58) Field of Classification Search
CPC .. A61L 9/12; A61L 2209/15; A61L 2209/134; A61L 31/146; A61L 9/04;
       (Continued)

(56) References Cited

U.S. PATENT DOCUMENTS 2,564,860 A * 8/1951 Ryberg .................. A45D 37/00
                                    239/54
4,157,787 A     6/1979 Schwartz
       (Continued)

FOREIGN PATENT DOCUMENTS

DE     102012204710 A1    9/2013
EP         1082969 A1     3/2001
       (Continued)

OTHER PUBLICATIONS

International Search Report and Written Opinion dated Mar. 16, 2020 from PCT International Appln. No. PCT/EP2019/086380.

*Primary Examiner* — Christopher R Dandridge

(74) *Attorney, Agent, or Firm* — Amster, Rothstein & Ebenstein LLP

(57) ABSTRACT

The device for diffusing volatile substances includes a container which contains a material with said volatile substances, a porous diffuser which is impregnated with said material with the volatile substances, and a protective sheet which is removed before the first use of the diffusion device. The device also includes a barrier layer equipped with a window, with said barrier layer joined to the container and placed between the porous diffuser and the protective sheet. Due to the presence of the window, the volatile substances are diffused at a high diffusion rate from the moment the protective sheet is removed.

11 Claims, 1 Drawing Sheet

(51) Int. Cl.

| | |
|---|---|
| B32B 1/00 | (2006.01) |
| B32B 3/26 | (2006.01) |
| B32B 7/05 | (2019.01) |
| B32B 7/06 | (2019.01) |
| B32B 15/08 | (2006.01) |
| B32B 27/08 | (2006.01) |
| B32B 27/10 | (2006.01) |

(52) U.S. Cl.
CPC ................. *B32B 1/00* (2013.01); *B32B 3/266* (2013.01); *B32B 7/05* (2019.01); *B32B 7/06* (2013.01); *B32B 15/08* (2013.01); *B32B 27/08* (2013.01); *B32B 27/10* (2013.01); *B32B 2250/44* (2013.01); *B32B 2260/028* (2013.01); *B32B 2260/04* (2013.01); *B32B 2307/718* (2013.01); *B32B 2307/724* (2013.01); *B32B 2307/7242* (2013.01); *B32B 2307/732* (2013.01); *B32B 2307/748* (2013.01); *B32B 2439/40* (2013.01)

(58) Field of Classification Search
CPC ................. A61L 9/01; A61L 2209/131; A61L 2209/133; A01M 1/2055; A01M 1/2044; Y10S 261/88; Y10S 428/905
See application file for complete search history.

(56) References Cited

U.S. PATENT DOCUMENTS

| | | | | |
|---|---|---|---|---|
| 5,050,798 | A | 9/1991 | Sullivan | |
| 5,234,162 | A * | 8/1993 | Sullivan | A61L 9/122 239/57 |
| 5,845,847 | A * | 12/1998 | Martin | A61L 9/12 239/58 |
| 2009/0148142 | A1 | 6/2009 | McGee et al. | |
| 2016/0000957 | A1* | 1/2016 | Dobler | A61L 2/00 239/34 |
| 2017/0107450 | A1* | 4/2017 | Frankenbach | C11B 9/00 |

FOREIGN PATENT DOCUMENTS

| | | | | | |
|---|---|---|---|---|---|
| FR | | 3039408 | A1 * | 2/2014 | A01M 1/2027 |
| WO | WO-2017115288 | | A1 * | 7/2017 | A61L 9/042 |

* cited by examiner

FIG. 1
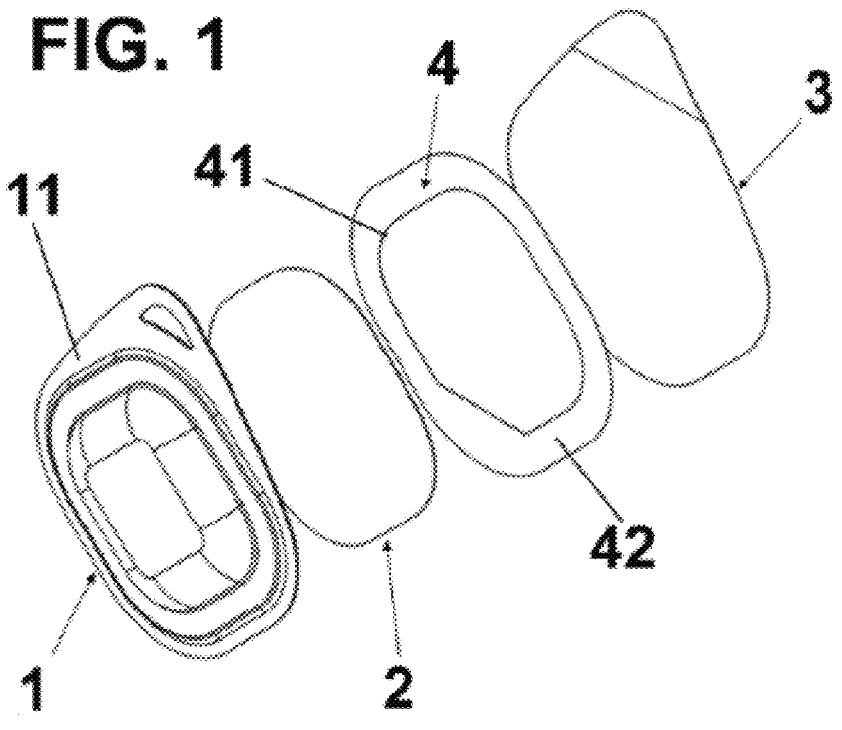
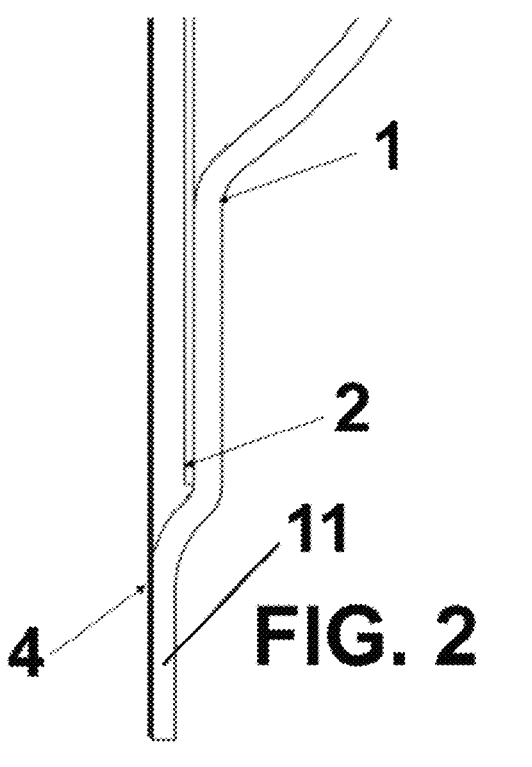
FIG. 2

DEVICE FOR DIFFUSING VOLATILE SUBSTANCES

CROSS-REFERENCE TO RELATED APPLICATIONS

This application is a U.S. national stage entry under 35 U.S.C. § 371 of PCT International Patent Application No. PCT/EP2019/086380, filed Dec. 19, 2019, which claims priority to Spanish Patent Application No. P201831264, filed Dec. 21, 2018, the contents of each of which are hereby incorporated by reference in their entirety.

The present invention relates to a device for diffusing volatile substances, comprising a container and a protective sheet which is removed from the container in order to enable the diffusion of said volatile substances.

BACKGROUND OF THE INVENTION

Devices that consist of a container with an active ingredient in solid, liquid or gel form for diffusing volatile substances, for example, insecticides or aromatic substances, into the air are well known in the state of the art.

Said active ingredient is typically separated from the outside of the container by a semi-permeable membrane barrier, or porous diffuser, which enables the active ingredient to pass through the semi-permeable membrane in a gaseous state, diffusing into the air.

One of the drawbacks of the currently-known solutions is that, since the semi-permeable barriers only enable the active ingredient to pass through in a gaseous state, controlling the rate of release of the active ingredient, they do not enable a sufficient quantity of the volatile substances to pass through the semi-permeable barrier without a significant increase in surface area.

This small quantity of volatile substances passing through the semi-permeable barrier prevents users from noting the presence of volatile substances during the first few minutes or hours of activation. Likewise, said semi-permeable barrier hinders the passage of larger volatile substances, restricting the use thereof to certain types of compounds with the appropriate size.

Furthermore, the semi-permeable barriers have a small absorption capacity, which leads to a low diffusion rate of volatile substances during the activation phase of the semi-permeable barrier.

Moreover, the devices for diffusing volatile substances that consist of materials pre-impregnated with an active ingredient for diffusion into the air are generally limited to the quantity of liquid that the material can absorb.

Therefore, one objective of the present invention is to provide a device for diffusing a large range of volatile substances in terms of size, wherein the volatile substances are diffused at a high rate of diffusion from the moment the protective sheet is removed and, at the same time, prevents the material with the volatile substances from accidentally exiting the container.

DESCRIPTION OF THE INVENTION

The device for diffusing volatile substances of the present invention resolves the aforementioned drawbacks, presenting other advantages that are described below.

The device for diffusing volatile substances according to the present invention comprises:

a container which contains a material with said volatile substances, a porous diffuser which is impregnated with said material with the volatile substances, and a protective sheet which is removed before the first use of the diffusion device, wherein the device also comprises a barrier layer equipped with a window, with said barrier layer joined to the container and positioned between the porous diffuser and the protective sheet.

Thanks to the presence of the window, the volatile substances are diffused at a high diffusion rate from the moment the protective sheet is removed.

Furthermore, the barrier layer prevents the material with the volatile substances from accidentally exiting the container.

Advantageously, said container comprises a perimeter edge, with said barrier layer joined on said perimeter edge.

Furthermore, advantageously, said window is cut into said barrier layer and defines a frame in said barrier layer.

Preferably, said barrier layer is made of plastic, although it could be made of any material that prevents the passage of material with said volatile substances.

According to one embodiment, the porous diffuser is made of cellulose, for example, with a thickness of between 0.4 and 0.6 mm, and a weight between 225 g/m² and 400 g/m².

Furthermore, the protective sheet is preferably made of aluminium, although it could be made of any suitable material to prevent the evaporation or diffusion of the volatile substances before it is removed, before the first use of the diffusion device.

Preferably, the container is made of thermoformed plastic, although it could be made of any other material suitable to contain the material with the volatile substances, which is, for example, a gel or liquid.

If desired, the barrier layer can be joined to the porous diffuser, by any suitable method, for example, by fusing.

BRIEF DESCRIPTION OF THE DRAWINGS

To provide a better understanding of the description, a series of drawings are included that schematically, and solely as an example and not for the purposes of limitation, represent a practical embodiment of the invention.

FIG. 1 is an exploded view of the device for diffusing volatile substances according to this invention; and FIG. 2 is a cross-sectional view of one end of the device for diffusing volatile substances according to the present invention, with the protective sheet removed.

DESCRIPTION OF A PREFERRED EMBODIMENT

As shown in FIG. 1, the device for diffusing volatile substances, for example, volatile aromatic substances or insecticides, comprising a container 1 which contains a material with said volatile substances, a porous diffuser 2 which is impregnated with said material with the volatile substances, and a protective sheet 3 which is removed before the first use of the diffusion device.

Furthermore, the diffusion device according to the present invention also comprises a barrier layer 4 equipped with a window 41, with said barrier layer 4 joined to the container 1 and placed between the porous diffuser 2 and the protective sheet 3.

Said window 41 is cut into said barrier layer 4 and defines a frame 42 in said barrier layer 4. That is, before removal of protective sheet 3, the barrier layer 4 has a cut line that separates the window 41 from frame 42, with the window 41 covered by a part of the barrier layer 4 which is removed together with the protective sheet 3 when the device is activated. This configuration of the barrier layer 4 is to facilitate the manufacture thereof, although it could be done in a different manner.

Said barrier layer 4 prevents accidental spillage or leakage of the material which contains the volatile substances, which is a gel or liquid, as well as the porous diffuser 2 element, while said window 41 enables the volatile substances to diffuse at a high rate of evaporation or diffusion.

As shown in said FIG. 1, on the barrier layer 4, said window 41 defines an outer frame, that is, the window 41 occupies most of the surface of said barrier layer 4.

Said container 1 for the active ingredient or material which contains the volatile substances may be made of a thermoformed plastic, for example, polyethylene (PE), polypropylene (PP), polyethylene terephthalate (PET).

This container 1 is formed or moulded in such a manner that it is arranged in a horizontal position, such that it can be filled from a vertical nozzle that can be positioned on top.

The container 1 comprises a perimeter edge 11 on which the barrier layer 4 is fastened, and this barrier layer 4, if desired, may also be fastened to the diffuser 2, although it could also be placed on the diffuser 2 without being fastened to it.

The diffuser 2 is made of a porous material with a high absorption capacity, which is impregnated with the active ingredient. In this manner, when, during its manufacture, it is placed under the protective sheet 3 and in direct contact with barrier 4, and on the container 1, the diffuser 2 is impregnated and saturated with the active ingredient from container 1. In other possible configurations, the diffuser 2 may be sealed to container 1 and/or the barrier layer 4.

The objective is that once the protective sheet 3 is removed, the diffuser 2, due to the high absorption rate of the porous material thereof, will be completely saturated and impregnated with a significant quantity of active ingredient.

The materials that can be used for this diffuser 2 may be cellulose paper with different thicknesses, non-fabric materials (such as polyethylene, polypropylene, etc.) formed into sheets with different thicknesses. Between the cellulose sheets, it may vary in thickness, for example, 0.4 and 0.6 mm, and a weight between 225 $g/m^2$ and 400 $g/m^2$.

The protective sheet 3 consists of a thin material that can be removed and discarded once the end user activates the device for the first use thereof. This material may be, but is not limited to, aluminium foil, EVOH, and similar materials.

The barrier layer 4 consists of a thin material that can be fused, laminated or bonded directly to the surface of thermoformed plastic container 1. This barrier layer 4 is cut prior to the operation coupling it to the container 1 in order to form the window 41.

In this manner, when the protective sheet 3 is removed, the barrier layer 4 remains joined to the container 1, which is a means of holding diffuser 2 and preventing direct leakage of the active ingredient. This barrier layer 4 may be, but is not limited to, polyethylene.

There may be joining elements between the protective sheet 3 and the barrier layer 4 in order to facilitate the lamination thereof or between the barrier layer 4 and the container 1. These connection elements could be, but are not limited to, polyolefins, resins, and similar materials.

Two specific examples of the device for diffusing volatile substances according to the present invention are described below.

According to the first example, the container 1 is made of thermoformed PP/PET plastic, with a thickness between 0.4 and 0.7 mm, which will be formed with three differentiated surface levels.

In container 1, there is a medium-high viscosity gel filler, with fragrance as the principal active ingredient that is diffused into volatile substances.

The diffuser 2 is made of cellulose with a thickness between 0.4 and 0.6 mm, and a weight of between 225 $g/m^2$ and 400 $g/m^2$. The barrier layer 4 is made of polyethylene and the protective sheet 3 is made of aluminium.

The container 1 is filled with the gel. This gel impregnates and saturates the cellulose diffuser 2. The assembly of the protective sheet 3 and the barrier layer 4 are then fused to the container 1, sealing it.

Since the barrier layer 4 comprises a window 41 cut out previously, when the protective sheet 3 is removed, the frame 42 of the barrier layer 4 remains joined to container 1, leaving said window 41, through which the fragrance (volatile substance) impregnated in the diffuser 2 will immediately begin to evaporate.

According to a second example, the container 1 is made of thermoformed PP/PET plastic, with a thickness between 0.4 and 0.7 mm, which will be formed with three differentiated surface levels, which is filled with a liquid or low-viscosity gel, with fragrance as the principal active ingredient, in the form of volatile substances.

The diffuser 2 is made of cellulose with a thickness between 0.4 and 0.6 mm, and a weight of between 225 $g/m^2$ and 400 $g/m^2$, with a barrier layer 4 made of polyethylene and a protective sheet 3 made of aluminium.

The main difference from the first example is that barrier layer 4 is fused not only to container 1, but is also partially fused to the diffuser 2. In this manner, the liquid, or low-viscosity gel, will be retained inside the container, with no risk of leakage.

Although reference has been made to a specific embodiment of the invention, it is clear for a person with skill in the art that numerous variations and modifications may be made to the device for diffusing volatile substances described, and that all of the details mentioned may be substituted with other technically equivalent details, without falling outside the scope of protection defined by the attached claims.

The invention claimed is:

1. A device for diffusing volatile substances, comprising:
   a container which contains a material with said volatile substances, the container including an interior edge;
   a porous diffuser which is impregnated with said material with the volatile substances;
   a protective sheet which is removed before a first use of the diffusion device; and
   a barrier layer equipped with a window, with said barrier layer joined to the container and placed between the porous diffuser and the protective sheet;
   wherein:
   an edge of the porous diffuser is provided about the interior edge of the container, between the barrier layer and the container, the porous diffuser being sealed to said barrier layer and to the container;
   said window is cut into said barrier layer and occupies most of said barrier layer to define an outer frame in said barrier layer; and
   before removal of the protective sheet, the barrier layer has a cut line that separates the window from the frame, with the window covered by a part of the barrier layer.

2. The device for diffusing volatile substances according to claim 1, wherein the container comprises a perimeter edge, with said barrier layer sealed on said perimeter edge along the whole perimeter of the container.

3. The device for diffusing volatile substances according to claim 1, wherein the barrier layer is made of plastic.

4. The device for diffusing volatile substances according to claim 1, wherein the porous diffuser is made of cellulose.

5. The device for diffusing volatile substances according to claim 1, wherein the porous diffuser has a thickness of between 0.4 and 0.6 mm, and a weight between 225 $g/m^2$ and 400 $g/m^2$.

6. The device for diffusing volatile substances according to claim 1, wherein the protective sheet is made of aluminium.

7. The device for diffusing volatile substances according to claim 1, wherein the container is made of thermoformed plastic.

8. The device for diffusing volatile substances according to claim 1, wherein said material with the volatile substances is a gel or a liquid.

9. The device for diffusing volatile substances according to claim 1, wherein said porous diffuser is directly fused to the barrier layer.

10. The device for diffusing volatile substances according to claim 4, wherein the porous diffuser has a thickness of between 0.4 and 0.6 mm, and a weight between 225 $g/m^2$ and 400 $g/m^2$.

11. The device for diffusing volatile substances according to claim 1, wherein said porous diffuser is directly fused to the barrier layer.

\* \* \* \* \*